US005753183A

United States Patent [19]
Ohr et al.

[11] Patent Number: 5,753,183
[45] Date of Patent: *May 19, 1998

[54] METHYL IODIDE AS A FUMIGANT

[75] Inventors: Howard D. Ohr; Nigel M. Grech; James J. Sims, all of Riverside, Calif.

[73] Assignee: The Regents of the University of California, Oakland, Calif.

[*] Notice: The term of this patent shall not extend beyond the expiration date of Pat. No. 5,518,692.

[21] Appl. No.: 649,555

[22] Filed: May 17, 1996

Related U.S. Application Data

[63] Continuation-in-part of Ser. No. 483,410, Jun. 7, 1995, Pat. No. 5,518,692, which is a continuation-in-part of Ser. No. 326,632, Oct. 20, 1994, abandoned.

[51] Int. Cl.$^6$ .................................................. B01J 19/00
[52] U.S. Cl. ........................ 422/37; 43/125; 47/DIG. 10; 422/1; 422/32; 422/40; 424/405
[58] Field of Search .......................... 422/1, 28, 32, 422/37, 40; 47/DIG. 10, 58; 43/125; 424/405, 667; 514/743

[56] References Cited

U.S. PATENT DOCUMENTS

| | | | |
|---|---|---|---|
| 2,403,435 | 1/1946 | Hammer | 167/39 |
| 2,407,333 | 10/1946 | Wenck et al. | 167/39 |
| 2,543,580 | 12/1951 | Kay | 167/39 |
| 2,794,727 | 5/1957 | Barrons | 71/2.7 |
| 2,875,118 | 2/1959 | Turner | 167/22 |
| 2,895,872 | 7/1959 | Meuli | 167/39 |
| 3,511,638 | 5/1970 | Joo et al. | 71/109 |
| 3,837,304 | 9/1974 | Carroll . | |
| 3,876,761 | 4/1975 | Shepherd | 424/78 |
| 3,961,050 | 6/1976 | Stach . | |
| 3,979,179 | 9/1976 | Teng | 21/60.5 |
| 4,819,374 | 4/1989 | Gemgnani . | |
| 4,882,321 | 11/1989 | Maurer et al. . | |
| 4,995,190 | 2/1991 | Royer . | |
| 5,202,047 | 4/1993 | Corby | 252/106 |
| 5,518,692 | 5/1996 | Grech et al. | 422/37 |

OTHER PUBLICATIONS

USDA Workshop on Alternatives for Methyl Bromide Jun. 29–Jul. 1, 1993, Doubletree Hotel Crystal City, VA. U.S. Dept of Agriculture.

The Biologic and Economic Assessment of Methyl Bromide (NAPIAP) National Agricultural Pesticide Impact Assessment Program, U.S. Dept. of Agriculture.

Methyl Bromide Alternatives Conference, United Nations Environment Programme, Nov. 1992.

Pyle, J.A., et al., In: *Scientific Assessment of Ozone Depletion*, eds. Albritton, D.L., et al., World Meteorol. Org., Geneva (1991), pp. 6.1–6.19.

Yagi, K., et al., "Agriculture Soil Fumigation as a source of atmospheric methyl bromide", PNAS USA 90:8420–8423 (1993).

Rolston, D.E., et al., "Comparisons of Simulated with Measured Transport and Transformation of Methyl Bromide Gas in Soils", *Pesticide Science* 13:653–664 (1982).

Price, N.R., "The Mode of Action of Fumigants", *J. Stored Prod. Res.* 21(4):157–164 (1985).

Lindgren, D.L., *J. Economic Entomol.* 31:320 (1938).

Lindgren, D.L., et al., "Relative Effectiveness of Ten Fumigants Adults of Eight Species of Store–Product Insects", *J. Economic Entomol.* 47:923–926 (1954).

Lehman, R.S., "Laboratory Tests of Organic Fumigants for Wireworms", *J. Economic Entomol.* 35:596–661 (1942).

Rajendran, S., et al., Delayed Mortality of Some Stored Product Insects Exposed to Candidtae Fumigants, *Indian. J. Ent.*, 49(3):363–369 (1987).

Hassall, K.A., "Relationships Between the Chemical Constituteion and Fu migant Toxicity of hte Alkyl Iodides", Ann. Appl. Biol. 43:615–629 (1955).

Lovelock, J.E., et al., "Halogenated Hydrocarbons in and over the Atlantic", Nature 241.:194–196 (1973).

Chameides, W.L., et al., "Iodine: Its Possible Role in Tropospheric Photochemistry", J. Geophys. Res. 84(12):7383–7398 (1980).

Rassmussen, R.A., et al., "Atmospheric Methyl Iodide ($CH_3I$)", J. Geophys. Res. 87(C4):3086–3090 (1982).

Korzh, V.D., "Ocean as a Source of Atmospheric Iodine", Atmospheric Environ. 18(12):2707–2710 (1984).

Jeffers, S.N., et al., "Comparison of Two Media Selective for *Phytophthora* and *Pythium* Species", Plant Disease 70:1038–1043 (1986).

Ko, et al., "A Selective Medium for the Quantitive Determination of *Rhizoctonia silani* in Soil", Phytopathology 61:707–710 (1971).

Plant Pathologists Pocketbook (1968) Commonwealth Mycological Institute, p. 239.

Melampy, R.M., et al., "Methyl Iodide as a Fumigant", J. of Econ. Entomol., 31:320 (1938) (Enclosed).

*Primary Examiner*—Krisanne M. Thornton
*Attorney, Agent, or Firm*—Townsend and Townsend and Crew

[57] ABSTRACT

Methyl iodide is employed as a structural fumigant for the effective control of soil borne and structural pests such as wood rotting fungi, arthropods such as insects and arachnids. Methyl iodide is employed in substantially the same manner as is customary for use of methyl bromide, and is at least as effective as methyl bromide when used in comparable amounts.

9 Claims, No Drawings

METHYL IODIDE AS A FUMIGANT

This application is a continuation-in-part application of co-pending U.S. patent application Ser. No. 08/483,410, filed Jun. 7, 1995, now U.S. Pat. No. 5,518,692, which in turn is a continuation-in-part of U.S. patent application Ser. No. 08/326,632, filed Oct. 20, 1994 now abandoned.

BACKGROUND OF THE INVENTION

The present invention relates generally to the fields of biology and agriculture. More particularly, the present invention relates to compositions and methods for use in fumigation of soils and structures.

The control of plant pathogens, nematodes and weeds is of central importance to the agriculture industry. In particular, the substantial reduction or complete elimination of nematode populations in soils is critical to initial plant growth, productivity and life-span. Pathogenic fungi and nematodes develop on the extensive root systems of both annual and perennial crops, damaging them severely. Moreover, they persist in the soil after crop removal and need to be eliminated before replanting of new crops. Among the fungi and nematodes of particular significance to agriculture are the following: root rot pathogens (Phytophthora spp., Pythium spp., Rhizoctonia spp., Fusarium spp.); vascular wilt pathogens (Verticillium spp., Fusarium spp.); root knot nematodes (Meloidogyne spp.); root lesion nematodes (*Pratylenchus vulnus*); ring nematodes (*Circonemella xenoplax*); stubby root nematodes (Paratrichodorus spp.); stem and bulb nematodes (*Ditylenchus dipsaci*); cyst nematode (*Heterodera schachtii*); citrus nematode (*Tylenchulus semipenetrans*) and the burrowing nematode (*Radopholus similus*).

To date, the only approaches which have been used successfully to combat plant pathogens and nematodes have been crop rotation or fallowing for at least four years, use of pathogen and nematode-resistant crops and soil fumigation. Rotation has limited value for control in many cases, because of the wide host range of many species of fungi and nematodes; moreover, many of the non-host crops provide only a low per acre return. Resistance to plant pathogens and nematodes is available only in a few crops, and resistant cultivars may not be developed in the foreseeable future for many crops of significant commercial interest. Therefore, soil fumigation remains the best alternative for control of plant pathogens and nematodes.

Methyl bromide ($CH_3Br$) is extremely important to United States agriculture {U.S.D.A. *The Biological and Economic Assessment of Methyl Bromide*, U.S.D.A. Publication (1993)}. It is the most widely used and most effective universal fumigant in the world. It is used extensively for soil fumigation, as a commodity quarantine treatment (export and imports) to control a variety of pests on numerous crops, and as a structural fumigant for wood destroying pests.

According to the Montreal protocol of 1991 (as amended in 1992), methyl bromide (hereinafter referred to as "MBr") was categorized as an ozone depleting chemical with an ozone depleting potential (ODP) of greater than 0.2 compared to trichlorofluoromethane (cfc 11), a refrigerant used as a reference gas having an ODP of 1. Title Five of the Clean Air Act (Stratospheric Ozone Protection), which was added in the 1990 amendments thereto, indicates in Section 602 that the U.S. Environmental Protection Agency (EPA) must list as a Class 1 ozone depleter any substance with an ODP of 0.2 or greater. Once designated, all production must be phased out by the year 2000. MBr has an ODP of 0.7; 30–40% of total ozone depletion is said to be as a result of bromine radicals, which are 30–60 times more efficient ozone depleters than chlorine {Pyle, J. A., et al., In: *Scientific Assessment of Ozone Depletion*, eds. Albritton, D. L., et al., World Meteorol. Org., Geneva, pp. 6.1–6.19 (1991)}.

Evidence on the loss of MBr to the atmosphere after soil fumigation indicates that of the total amount applied to the soil for fumigation, approximately 87% is lost to the atmosphere within seven days {Yagi, K., et al., *PNAS USA*, 90:8420–8423 (1993)}. On reaching the stratosphere MBr undergoes photo-oxidation, releasing bromine atoms which enter the ozone depletion cycle. MBr loss from fumigated soils is further supported by studies which indicated a loss of as much as 70% of the applied MBr to the atmosphere through the tarp and after the tarp is removed {Rolston and Glauz, *Pesticide Science* 13:653 (1982)}.

In 1990, approximately 64,000,000 pounds of MBr were used in the U.S., of which 44–49 million pounds were used for soil fumigation (control of insects, nematodes, weeds, plant pathogenic microbes and vertebrate and invertebrate pests), 5 million for post harvest and quarantine treatments, 4–9 million pounds for fumigating structures and 6 million pounds for use as chemical intermediates. Thus, approximately 80% of the total is used for agriculturally related purposes.

As currently available alternatives to MBr are less effective and/or more expensive, the removal of MBr will be very costly. Annual losses to U.S. producers and consumers is estimated to be in the region of 1.5 billion dollars. This figure does not account for the losses due to post harvest and quarantine losses as well as structural fumigation losses. California and Florida are the largest users of MBr (approximately 25,000,000 pounds combined) in the U.S., and hence will be most heavily affected by its removal. MBr removal would most adversely affect such commodities as tomatoes, strawberries, peppers, melons and ornamentals. The loss of MBr would thus be extremely costly to both agricultural producers and consumers as well as having a substantial impact on the U.S. economy. Nonetheless, it is the general consensus of those working in the field that no approach is currently available that will achieve the same level of broad-spectrum pest management as MBr; chemical and non-chemical approaches that are available can provide some level of agricultural pest management, but generally with narrower activity and lower crop yields and quality. Therefore, there is clearly a need for alternatives to MBr.

MBr has been used as an insecticidal fumigant since the 1930s {Bond, F. J., *Manual of fumigation for insect control*, Plant Product Protection Papers No. 54, Food and Agriculture Organization (FAO), Rome (1989)}. Application of MBr for control of structural pests began in southern California more than 40 years ago, primarily against the western drywood termite, *Incisitermes minor* (Hagen) {Hunt, R. W., *J. Econ. Entomol*, 42:959–962 (1949)}. Currently, MBr is registered in the United States for use against various wood and household pests. However, drywood termites (Kalotermitidae), which occur throughout much of the southern and western United States, remain the primary targets of structural fumigations. Scheffrahn, et al. compared the toxicity of MBr against ten nearctic termite species and found that current commercial label rate recommendation for MBr are considerably higher than required {Scheffrahn, R. H., et al., *J. Econ. Entomology*, 85(3):845–847(1992)}. Typically, liquid MBr is heated to a gas before introduction within a tarpaulin-enclosed building. The duration of the MBr exposure period is variable, but for convenience of occupants and applicators (and to accumulate sufficient exposure time), most fumigations with MBr are done for 20–24 hours.

It is an object of the present invention to provide methods and compositions for use in soil and structural fumigation which ameliorate at least some of the problems attendant to prior art methods.

SUMMARY OF THE INVENTION

In accordance with the present invention, methyl iodide (hereinafter referred to as "MI") is employed as a soil and structural fumigant for the effective control of: (1) soil borne plant pathogens such as fungi, bacteria, viruses, and nematodes in the case of soil fumigation; and (2) soil borne and structural pests such as wood rotting fungi, arthropods such as insects and arachnids (including their eggs, larvae, and pupae), in particular household pests such as termites, lyctid beetles, cockroaches, carpenter ants, mites, fungal gnat larvae, animal parasites, and spiders in the case of soil and structural fumigation. MI may be employed in substantially the same manner as is customary for use of MBr, and is at least as effective as MBr when used in comparable amounts.

DETAILED DESCRIPTION OF THE INVENTION

The abbreviations used in this application are as follows:

| | |
|---|---|
| C. brevis | Cryptotermes brevis |
| MBr | methyl bromide |
| MI | methyl iodide |
| LAD | Lethal Accumulated Dose |
| ODP | ozone depleting potential |
| UV | ultraviolet |
| UVB | ultraviolet B |
| UVC | ultraviolet C |

While the present invention is not bound to any particular theory, MI appears to be totally analogous to MBr in its ability to act as a biocide. The generally accepted mechanism explaining the activity of a member of the lower alkyl halide series is that it reacts via bimolecular nucleophilic displacement ($S_N2$) reaction with functional groups such as $NH_2$ and SH in various amino acids and peptides in target organisms {Price, N. R., *J. Stored Prod. Res.*, 21(4):157–164 (1985)}. MI reacts at approximately the same rate as MBr under most $S_N2$ conditions that have been reported.

There have been several reports in the literature of the use of MI as a fumigant for control of insect populations in stored grain {Lindgren, D. L., *J. Economic Eiitomnol.*, 31:320 (1938); Lindgren, D. L., et al., *J. Economic Entomol.*, 47:923–926 (1954); Lehman, R. S., *J. Economic Entomol.*, 35:659–661 (1942); Rajendran, S., et al., *Indian J. Ent.*, 49(3):363–369 (1987); Hassall, K. A., *Ann. Appl. Biol.*, 43:615–629 (1955)}. Nonetheless, it would simply not have been possible to predict that an agent having utility in control of insect populations in stored grain would in fact have any utility whatsoever in fumigation of soils for elimination of plant pathogens, nematodes, bacteria and/or weeds.

Soil can modify the chemical activity of fumigants. Whereas activity of an agent may be high in air, it may have much less activity in soil {Lehman, R. S., *J. Economic Entomology*, 35:659–661 (1942)}. Indeed, fumigation of stored grain and its expectations are relatively simple when compared to the complexity of fumigating soils and the expectations from such fumigations. Humidity in stored grain is uniform throughout the product, whereas in soil it can vary greatly. In addition, particle size in stored grain is fairly uniform, as are the airspaces between particles; this makes fumigation of grain relatively simple. In soil, the particle sizes and airspaces vary widely, substantially complicating fumigation.

Further, the target organisms in stored grain are fairly limited in variety and quite different from the large variety and number of target organisms in the soil. Fumigation in stored grain targets insects; fungi, nematodes and bacteria are not usually a problem when the humidity is kept low,and weeds would not be affected by a fumigation that did not also kill the grain. In soil, fumigation is expected to kill fungi, nematodes, weed seeds, insects, and vertebrate and invertebrate pests.

As a consequence, many fumigants used for stored products are generally not used as soil fumigants. For example, phosphine is currently registered and used for stored products but not used in soil where it is apparently ineffective. Some pests are resistant to phosphine, and it is not effective under 50° F.; moreover, it requires a fumigation time of 3–5 days and is highly flammable. Similarly, esters of formate (e.g., methyl formate) are effective in treating stored products, but are much less effective in soil. Therefore, it is clear that compositions useful as stored products fumigants are not necessarily useful as soil fumigants. Structural fumigation concerns fumigation of buildings. Generally, buildings are made of wood, plaster, bricks, etc. and/or mixture thereof. Stored product fumigation is relatively simple when compared to structural fumigation. Stored products are normally of a single consistency, i.e. grain, and as such has a uniform structure, air spaces, and humidity. As such, a fumigant would be expected to penetrate uniformly. Structural fumigation encounters objects and spaces of different sizes, different humidities, different consistency, and different composition. Therefore, a fumigant used for stored product fumigation may not be the best one to use for structural fumigation. The finding in this application that MI behaves similarly to MBr in its dispersion properties and that its efficacy is as good as or better than MBr would indicate that it would be a good structural fumigant.

In trials carried out in accordance with the invention, MI has proven to be an effective chemical for the fumigation of five species of soil borne plant pathogenic fungi, one saprophytic fungus, three weeds and two nematodes. In the majority of trials in both the laboratory and the field, MI was effective at rates that were equivalent to 0.5 to 1.0 lb of MBr per 100 ft³. In only one trial, on one fungus, for unknown reasons MI did not eliminate the fungus at any rate (TABLE 3); however, this fungus was eliminated in a different trial (TABLE 2). In direct comparison field trials MI was as effective as MBr (TABLES 7 and 8) in eliminating the pathogen. In three laboratory trials, MI was more effective as a soil fumigant than seven other alkyl iodides. Therefore, MI is at least as effective as MBr in fumigating soil to eliminate soil borne plant pathogenic fungi.

In trials carried out according to this invention, MI has proven to be as effective or more effective than currently used structural fumigants in killing termites, beetle eggs, and wood rotting fungi. In particular, MI was compared to MBr in a series of laboratory trials to determine its effectiveness against termites (*Cryptotermes brevis*), Lyctid beetle eggs, and two wood rotting fungi (*Meruliporia incrassata* and *Gleophyllum separium*). The chemical can be applied using the same equipment currently used to apply MBr.

MI is a rapidly evaporating liquid at normal room temperatures that is safer to handle than MBr. MI has an atmospheric residence time of up to 8 days while that of MBr is 2 years.

MI has the further advantage over MBr in that it is an ozone safe alternative to MBr as a fumigant. MI absorbs UV radiation most strongly in the UVC range (100 to 280 nm) with a maximum approximating 260 nm, although strong absorption occurs at longer (UVB) wavelengths (280 to 315 nm). It is these which are believed to be responsible for tropospheric degradation. UV absorption causes photodegradation, leading to the formation of methyl radicals and iodine radicals.

The estimated lifetime of MI in the troposphere is between about 50 hours and about 8 days, as compared to MBr with an estimated atmospheric lifetime of 1.5 years {Lovelock, J. E., et al., Nature 241:194–196 (1973); Chameides, W. L., et al., J. Geophys. Res., 85(12):7383–7398 (1980)}. As a consequence, MI has not been intimated in stratospheric ozone depletion {Rassmussen, R. A., et al., J. Geophys. Res., 87(C4):3086–3090 (1982)}. MI has a vapor pressure of approximately 25% that of MBr and hence is less volatile, and has a similar solubility in water. Due to its rapid photolysis in the troposphere, MI (unlike MBr) is rapidly removed from the atmosphere. MI occurs at saturated levels in the ocean and is principally produced by marine algae {Chameides, et al., (1990), supra; Korzh, V. D., Atmospheric Environ., 18(12):2707–2710 (1984)}; it is postulated that this is the principal source of MI in the marine boundary layer. Levels of MI in the atmosphere adjacent to the marine boundary layer are usually 2.5 times lower {Korzh (1984), supra}.

As with other halogens, the postulated chemistry of iodine if it reached the stratosphere suggests that it would be very effective in ozone destruction {Rolston & Glauz (1982), supra}. However, the above reasons and the very short life of MI in the atmosphere negate the likelihood of any substantial migration of MI to the stratosphere. As the atmospheric life of MBr is approximately 1.5 years, it clearly has an ozone-depleting potential several orders of magnitude higher than MI. Studies on trifluoromethyl iodide have not shown any involvement of this substance with ozone depletion. This substance is similarly broken down by solar radiation to reactive radicals; as with $CH_3I$, it does not reach the stratosphere due in part to its short tropospheric half life.

Application of MI in accordance with the present invention may be effected by a number of different procedures as are currently routinely employed for soil and structural treatments with MBr. Thus, for example, MI may be applied to the soil by tractor mounted injectors on tynes, manually in canisters and via an existing irrigation system or as a gas through lay flat tubing. For example, for structural fumigation, liquid MI may be heated to a gas before introduction within a tarpaulin-enclosed building. Thus, MI may advantageously be pre-heated by passage through a heat exchanger prior to delivery; pre-heating vaporizes MI for more rapid and even distribution and increases its activity. In addition, MI may be dissolved in suitable solvents (e.g. lower alcohols, acetone, mixtures of water with acetone or alcohol, etc.) to assist in dispersion of the material in the soil. Further, it is contemplated as within the scope of the invention to apply mixtures of MI with other fumigants (e.g., carbon disulfide or chloropicrin) in ratios comparable to those currently employed with MBr. For example, a mixture of 67% MI and 33% chloropicrin would be effective, as would a mixture of about 98% MI with 2% chloropicrin as a warning agent. In structural fumigation, a mixture of about 98% MI with 2% chloropicrin as a warning agent is preferred. In general, it is preferred that tarping be undertaken immediately following fumigation. The duration of the fumigation treatment and the application and removal of tarps should be consistent with contemporary practice in connection with MBr treatments. For example, the duration of the MI exposure period may be variable, but for convenience of occupants and applicators (and to accumulate sufficient exposure time), the fumigation with MI is preferably done for 20–24 hours.

A wide range of application rates of MI have been found suitable in accordance with the present invention. Those working in the field would of course be readily able to determine in an empirical manner the optimum rates of application for any given combination of crops, soils, structures, and the target organisms to be killed or eliminated. In general, soil fumigation application of MI is preferably effected at a rate of about 2 lb/acre to about 2000 lb/acre (2.23 kg/hectare to about 2250 kg/hectare), more preferably about 500 lb/acre to about 1500 lb/acre (560 kg/hectare to about 1680 kg/hectare), and most preferably about 600 lb/acre to about 1200 lb/acre (670 kg/hectare to about 1340 kg/hectare). Applications of MI at rates substantially in excess of about 2000 lb/acre (2250 kg/hectare) would not be expected to provide any significant advantage over applications within the preferred ranges specified herein, but are nonetheless regarded as well within the scope of the present invention.

Soil fumigation with MI in accordance with the present invention has been found to be extremely effective in the substantial or complete elimination of a wide variety of plant pathogens. For purposes of the present invention, substantial elimination of a plant pathogen is intended to mean reduction in the population of the pathogen by about 90%, more preferably about 95%, and most preferably about 100%. In general, treatment in accordance with the present invention by application of an amount of MI within the preferred ranges specified herein results in almost complete elimination of plant pathogen populations within the present limits of customary means employed for the detection thereof.

Plant pathogenic organisms successfully controlled or eliminated by treatments in accordance with the present invention include, but are not limited to, nematodes, fungi and weeds. Particular plant pathogens and nematodes controlled or eliminated by application of MI include, but are not limited to, the following: root rot pathogens (Phytophthora spp., Pythium spp., Rhizoctonia spp., Fusarium spp.); vascular wilt pathogens (Verticillium spp., Fusarium spp.); root knot nematodes (Meloidogynespp.); root lesion nematodes (*Pratylenchus vulnus*); ring nematodes (*Circonemella xenoplax*); stubby root nematodes (Paratiichodorus spp.); stem and bulb nematodes (*Ditylenchus dipsaci*); cyst nematode (*Heterodera schachtii*); citrus nematode (*Tylenchulus semipenetrans*) and the burrowing nematode (*Radopholus similus*). While the definition of "weed" in agriculture is of course purely contextual, among the types of plants generally sought to be controlled or eliminated the following should be mentioned; cheeseweed (Malva spp.), field bindweed (*Convolvulus arvensis*), annual bluegrass (*Poa annua*), etc. MI treatment is also useful in the control of other pathogens, such as crown gall (*Agrobacterium tumefaciens*) and other plant pathogenic bacteria. Finally, as previously reported in the literature treatment with MI may also reduce or eliminate the populations of a variety of insects. Insects of particular interest in agriculture which are controlled or eliminated during a treatment in accordance with the present invention include, but are not limited to, the following: fungal gnat larvae, soil mealy bugs, phylloxera, ants, termites and animal parasites, etc.

As shown in the "EXAMPLES" section below, fungi, in particular wood rotting fungi, will generally require higher concentrations of MI for effective kill rate. Generally, for general structural fumigation (which would fumigate all targets of commercial structural fumigation, such as: termites and wood rotting fungi), the structural fumigation with MI is preferably effected at a rate of about 0.3 oz/1000 cu ft to about 100 lb/1000 cu ft (85 g/28.3 cubic meters to about 45.4 kg/28.3 cubic meters), more preferably about 8 oz/1000 cu ft to 50 lb/1000 cu ft (227 g/28.3 cubic meters to 22.7 kg/28.3 cubic meters), and most preferably about 1 lb/1000 cu ft to 10 lb/1000 cu ft (454 g/28.3 cubic meters to 4.54 kg/28.3 cubic meters). The abbreviation "cu ft" denotes cubic feet. Generally, for general structural fumigation (which would fumigate all commercial targets of structural fumigation such as termites and wood rotting fungi), the structural fumigation with MI is preferably effected at a rate of about 3 oz/1000 cu ft.

The efficacy of MI may also be increased by adding moderate heat and/or carbon dioxide. The amount of carbon dioxide to be added would be the same as those used for structural fumigation using MBr. Preferably 5% carbon dioxide is used. The temperature is preferably above 70° F.

The trials in this application show that structural fumigation with MI according to the present invention would be effective in the substantial or complete elimination of wood rotting fungi, insects, and insect eggs. For purposes of the present invention, substantial elimination of arthropods such as insects and arachnids (including their eggs, larvae, and pupae), and wood rotting fungi is intended to mean reduction in the population of these organisms by about 90%, more preferably about 95%, and most preferably about 100%. Generally, treatment according to the present invention by application of an amount of MI within the preferred ranges specified herein results in almost complete elimination of the populations of these organisms within the present limits of customary means employed for the detection thereof.

Wood rotting organisms successfully controlled or eliminated by structural fumigation treatments according to the present invention include, but are not limited to: wood rotting fungi such as *Meruliporia incrassata* and *Gleophyllum separium*. Pests which can be successfully controlled or eliminated by structure fumigation treatment according to the present invention include, but are not limited to: arthropods such as insects and arachnids (including their eggs, larvae, and pupae), in particular household pests such as termites (*Cryptotermes brevis, Incisitermes minor* (Hagen) and others), lyctid beetles, cockroaches, carpenter ants, mites, fungal gnat larvae, animal parasites, and spiders.

The above ranges are just general guides, in a specific situation. The following factors are to be taken into account.

For example, primary factors that may significantly alter the efficacy of MBr in the field are gas loss through the seal (substructure foundation and tarpaulin), decreased toxicity at lower temperature {Stewart, D., *J. Econ. Entomol.*, 50:7–11 (1957) and Kenaga, F. E., *J Econ. Entomol.*, 54:537–542 (1961)}, time lag for gas to reach diffusion equilibrium in the structural airspace, and substrate sorption and permeation. Diffusion equilibrium is accelerated by the use of high-output fans and can normally be attained within 2 hours in single-family homes. Because structures fumigated for termites are relatively empty of sorptive commodities, the only other factor that reduces MBr efficacy is permeation of the substrata that harbor termites. Thus, it is preferably that for structural fumigation, the MI be used at about 3 oz per 1000 cubic feet or more.

The invention may be better understood with reference to the accompanying examples, which are intended for purposes of illustration only and should not be construed as in any sense limiting the scope of the invention as defined in the claims appended hereto.

EXAMPLES

The following describes in detail the conditions of the soil fumigant studies in EXAMPLES 1–13, below. EXAMPLES 14–16 simulate structural fumigation.

Fungi used were maintained as stock cultures and transferred to 15 cm potato dextrose agar (PDA) petri plates as needed. Plate colonies were allowed to grow at ambient laboratory temperature (ca. 25° C.). When ¾ of the agar surface was covered the cultures were considered ready for use. Circular plugs, 18 mm in diameter, were cut from the leading edge of colony growth with a sterile cork borer and used to inoculate sterile millet seed.

Three hundred ml of white millet seed was placed in 950 ml (1 qt) Mason canning jars, rinsed with distilled water and drained. The jars were sealed with canning lids and rings. The lids had 12 mm holes plugged by non-absorbent cotton. The jar tops were then covered with a double layer of heavy brown paper secured by masking tape. The jars were placed in a deep, autoclavable plastic pan to which water was added until it passed the level of seed in the jars. The seed was sterilized for 30 min at 250° C. and 1 atm of pressure. After sterilizing, the seed was cooled to room temperature and 100 ml of a 1:9 sterile V-8 juice-water mixture was added to each jar. The millet was then inoculated with 10 circular agar plugs of the appropriate fungus and incubated at laboratory temperatures until used or discarded. Jars were shaken periodically to distribute the fungal growth. Seed not used within 30 days was discarded. For smaller amounts of inoculum, 100 ml of seed was used and incubated in 500 ml Erlenmeyer flasks. These flasks were sealed with a cotton plug and covered with aluminum squares.

When used, millet seed cultures were removed from the jars, broken up by hand into individual seeds and added to the appropriate soil for the experiment. The seed culture was thoroughly mixed into the soil at a ratio of 300 ml to 3.5 l of soil.

Soils used for inoculum were a 1:1 potting mix of topsoil and sawdust or wood shavings for the laboratory experiments and field soil sieved through a No. 10 screen for field trials. Moisture in the inoculum soil ranged from 8.4% to 32%, depending on the trial. Soils were sterilized by autoclave before adding inoculum.

Inoculum containers were made from 45 ml clear plastic vials (No. 55–12, Thornton Plastic Co., Salt Lake City, Utah). Each vial was perforated by sixteen 1 cm holes using an Unger electric soldering iron with ½ cm tip. The holes were distributed in two rows of 4 and two of three (on opposite sides) with one hole in the bottom and one in the white plastic snap cap.

After the vials were filled with inoculum, those used in laboratory trials were placed on a 1 cm layer of potting mix in 1893 ml (2 qt) Mason canning jars and covered with the same soil to a depth of 1 to 1 ½ cm. The jars were placed under a fume hood and a measured amount of the fumigant was injected into each jar using a micropipette with the appropriate tip. The fumigant was placed on the soil just inside the mouth of the jar. The jars were sealed immediately with a solid canning lid and ring and placed horizontally on the laboratory bench to incubate. Incubation was for 1, 2 or 3 days depending on the trial. Each experiment contained 4 replications of 25 seeds each per treatment.

After fumigation the vials were removed from the soil and ventilated under the hood for one hour. After ventilating the seed were separated from the soil by sieving through a No. 10 soil sieve. Twenty five seeds from each replicate were chosen and placed on agar in 15 cm petri plates. For Pythium spp. PARP medium was used, and for Phytophthora PARPH medium {Jeffers & Martin, *Plant Disease*, 70:1038–1043 (1986)}; for Rhizoctonia, a medium was used as reported in the literature {Ko & Hora, *Phytopathology*, 61:707–710 (1971)}. Other fungi were plated on ¼ strength PDA medium {Plant Pathologists Pocketbook, Commonwealth Mycological Institute, p. 239, (1968)}. After plating seeds were incubated at laboratory temperatures and surveyed for growth after were counted and the plates checked until no more growth appeared, usually 3–4 days. After the results were recorded the plates were disposed of by sterilization.

In field trials the inoculum was prepared as described above and placed at depths of 2.5, 15 and 30 cm half way between the center and one corner of each plot. The plots were 3×3 m and the corner for placement of the inoculum was chosen randomly. Field trials were block randomized with 4 replications per treatment. After the fumigant was applied the plots were covered with 4 mil clear polyethylene plastic sheeting with the edges buried 7 cm.

MBr was prepared by storing 454 g containers and laboratory glass beakers 14 h in a portable ice chest with frozen $CO_2$. When used, the treatment amount was measured, poured into a chilled beaker, placed on the soil surface in the center of the plot, and covered with an inverted 15 cm black plastic plant pot. MI was treated the same way but was not prechilled. The plot was then covered with plastic sheet. The control was no treatment covered with plastic. After 4 days the plastic was removed and the plots were allowed to aerate for 2 days. The inoculum vials were then removed and evaluated as described.

All fumigation concentrations were based on a MBr application rate of 0.454 kg/2.8 m$^3$ (1 lb/100 ft$^3$), equal to 4.78 moles/2.8 m$^3$ for field trials and 1.69 µM/ml for laboratory trials.

Example 1

This series of trials utilized *Phytophthora cinnamomi* and *Rhizoctonia solani* as the test organisms. MI concentrations used were 1.69, 1.27, 0.84 and 0.42 µM/ml. Fumigation time periods were 24, 48 and 72 hours.

In this series all non-treated controls for both Phytophthora and Rhizoctonia had a 100% recovery rate based on an average of 4 replications of 25 seeds each. Cultures of Phytophthora and Rhizoctonia fumigated 1 day at 0.42 µM/ml had recovery rates of 19% and 72%, respectively. After 2 days both had no recovery, while after 3 days at this concentration Rhizoctonia had a 1% recovery rate. All other concentrations were completely effective with no recovery of either fungus.

Example 2

This series of trials utilized *P. cinnamomi*, *R. solani* and *P. citrophthora* as the test organisms. MI concentrations were 1.69, 1.27, 0.84, 0.42 and 0.21 µM/ml. Fumigation time periods were 24, 48 and 72 hours.

Upon collecting data it was found that the Rhizoctonia culture was contaminated with an Aspergillus sp. so data was collected on that species. All non-treated controls for all three organisms for all three time periods were 100% viable. The lowest concentration of 0.21 µM/ml MI (=0.125 lb MBr/100 ft$^2$) was ineffective for all three time periods for *P. citricola* and the 1 day and 2 day periods for *P. cinnamomi* and Aspergillus sp. with 100% recovery. At 3 days at this concentration both *P. cinnamomi* and Aspergillus had a recovery rate of 55%. At 0.42 µM/ml MI (=0.250 lb MBr/100 ft$^2$) *P. citricola* had a 54% recovery after 1 day and 0 after 2 and 3 days, while *P. cinnamomi* had 65% at 1 day and 0 at 2 and 3 days; Aspergillus had 25% at 1 day and 0 after 2 and 3 days. At 0.84 µM/ml MI (=0.5 lb MBr/100 ft$^2$) there was no recovery of *P. citricola*, while *P. cinnamomi* had a 25% recovery after 2 days but 0 for day 1 and 3; Aspergillus had a 20% recovery after 1 day but 0 for days 2 and 3. Concentrations of MI at 1.27 µM/ml (=0.75 lb MBr/100 ft$^2$) and 1.69 µM/ml (=1.0 lb MBr/100 ft$^2$) for all time periods had 0 recovery (TABLE 1).

In all of the tables, numbers followed by different letters are significantly different at p=0.05 using the Duncan-Waller T test.

TABLE 1

| µM/ml MI | Days | Recovery % | Note |
|---|---|---|---|
| *P. citricola* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 100 | a |
| 0.42 | 1 | 54 | bc |
| 0.42 | 2 | 0 | d |
| 0.42 | 3 | 0 | d |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |

| ml MI | Days | Recovery % | Note |
|---|---|---|---|
| *P. cinnamomi* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.42 | 1 | 65 | b |
| 0.21 | 3 | 55 | bc |
| 0.84 | 2 | 25 | cd |
| 0.42 | 2 | 0 | d |
| 0.42 | 3 | 0 | d |
| 0.84 | 1 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| Aspergillus | | | |
| 0 | 1 | 100 | a |
| 0 | 2 | 100 | a |
| 0 | 3 | 100 | a |
| 0.21 | 1 | 100 | a |
| 0.21 | 2 | 100 | a |

TABLE 1-continued

| | | | |
|---|---|---|---|
| 0.21 | 3 | 55 | bc |
| 0.42 | 1 | 25 | cd |
| 0.84 | 1 | 20 | d |
| 0.42 | 2 | 0 | d |
| 0.42 | 3 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |

Example 3

This series of trials utilized *P. cinnamomi*, *P. citricola*, *P. parasitica* and *R. solani*. MI concentrations were 1.69, 1.27, 0.84, 0.42, and 0.21 µM/ml. Fumigation time periods were 24, 48 and 72 h.

Control recovery for *P. cinnamomi* was 100% at 1 day, 99% at 2 days and 100% at 3 days. The *P. cinnamomi* recovery rate at 0.21 µM/ml MI (=0.125 lb MBr/100 ft$^2$) was 62% after 1 day, 64% after 2 days and 62% after 3 days. At 0.42 µM/ml MI (=0.25 lb MBr/100 ft$^2$) the rate after 1 day was 39%, after 2 days 23% and after 3 days 5%. There was no recovery at the higher concentrations of MI at 0.84 µM/ml (=0.5 lb MBr/100 ft$^2$), 1.27 µM/ml (=0.75 lb MBr/100 ft$^2$) and 1.69 µM/ml (=1.0 lb MBr/100 ft$^2$) for any time period (TABLE 2).

For *P. citricola* recovery rates after 1 day were control 100%, 0.21 µM/ml MI 100%, 0.42 µM/ml MI 100%, 0.84 µM/ml MI and higher 0%. After day 2 the control was 100%, 0.21 µM/ml MI was 85%, 0.42 µM/ml MI was 4% with all higher concentrations 0%. After 3 days the control was 99%, the 0.21 µM/ml MI was 61% and all other concentrations were 0 (TABLE 2).

For *P. parasitica* recovery for the control, 0.21 and 0.42 µM/ml MI after 1 day were all 100% and all higher concentrations were 0. After 2 days the control and 0.21 µM/ml MI recovery was 100%, and at 0.42 µM/ml MI it was 54%; all other concentrations were 0. After 3 days exposure recovery of the control was 98%, 0.21 µM/ml MI was 100% and 0.42 µM/ml MI was 76%; all other concentrations were 0 (TABLE 2).

For Rhizoctonia after 1 day recovery was 100% for the control, 0.21 and 0.42 µM/ml MI and 29% for 0.84 µM/ml MI. All other concentrations were 0. After 2 days the control and 0.21 µM/ml MI were 100%, 0.42 was 93% and all other concentrations were 0. After 3 days the control and 0.21 µM/ml MI were recovered at 100% and 0.42 at 48%; all other concentrations were 0 (TABLE 2).

TABLE 2

| µM/ml MI | Days | Recovery % | Note |
|---|---|---|---|
| *P. citricola* | | | |
| 0 | 1 | 100 | a |
| 0 | 2 | 100 | a |
| 0 | 3 | 100 | a |
| 0.21 | 1 | 100 | a |
| 0.42 | 1 | 98 | a |
| 0.21 | 2 | 85 | ab |
| 0.21 | 3 | 61 | c |
| 0.42 | 2 | 4 | d |
| 0.42 | 3 | 0 | d |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| *P. cinnamomi* | | | |
| 0 | 1 | 100 | a |
| 0 | 2 | 100 | a |
| 0 | 3 | 100 | a |
| 0.21 | 2 | 72 | bc |
| 0.21 | 1 | 62 | c |
| 0.21 | 3 | 62 | c |
| 0.42 | 1 | 39 | c |
| 0.42 | 2 | 23 | d |
| 0.42 | 3 | 5 | d |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| *P. Parasitica* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 100 | a |
| 0.42 | 1 | 100 | a |
| 0.42 | 3 | 76 | ab |
| 0.42 | 2 | 54 | bc |
| 0.84 | 1 | 0 | d |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |
| *R. Solani* | | | |
| 0 | 1 | 100 | a |
| 0 | 2 | 100 | a |
| 0 | 3 | 100 | a |
| 0.21 | 1 | 100 | a |
| 0.21 | 2 | 100 | a |
| 0.21 | 3 | 100 | a |
| 0.42 | 1 | 100 | a |
| 0.42 | 2 | 100 | a |
| 0.42 | 3 | 48 | bc |
| 0.84 | 1 | 29 | c |
| 0.84 | 2 | 0 | d |
| 0.84 | 3 | 0 | d |
| 1.27 | 1 | 0 | d |
| 1.27 | 2 | 0 | d |
| 1.27 | 3 | 0 | d |
| 1.69 | 1 | 0 | d |
| 1.69 | 2 | 0 | d |
| 1.69 | 3 | 0 | d |

Example 4

These trials utilized *P. citrophthora*, *P. citricola*, *P. parasitica* and *R. solani*. MI concentrations were 1.69, 1.27, 0.84, 0.42, and 0.21 µM/ml. Fumigation time periods were 24, 48 and 72 hours.

After 1 day recovery of *P. citrophthora* was 100% for the control and 0.21 µM/ml MI. After 2 days control recovery was 100% and at 0.21 µM/ml MI it was 32%. After 3 days recovery was 100% for the control and 10% for 0.21 µM/ml MI. All other exposures were 0.

For *P. citricola* the control at 1 day exposure was recovered 100% and 0.21 µM/ml MI recovery was 33%. After 2 days recovery was 100% for the control, 1% for 0.21 µM/ml MI and 2% for both 0.84 and 1.69 µM/ml MI. After 3 days recovery for the control was 100%; recovery at all other exposures was 0.

For *P. parasitica* recovery in the control was 100% for all three time periods while at 0.21 µM/ml MI recovery at 1 day was 98% and at 2 days was 19%. All other exposures were 0.

In this trial recovery of Rhizoctonia was 100% for all three time periods for the control and 0.21 µM/ml MI and for 1 day of 0.42 µM/ml MI. Recovery at 2 days of 0.42 µM/ml MI was 32% and at 3 days was 91%. At 0.84 µM/ml MI recovery was 30%, 44% and 45% for 1, 2 and 3 days, respectively. At 1.27 µM/ml MI recovery was 17%, 43% and 68% for the same three time periods. At 1.69 µM/ml MI recovery was 20% at one day, 53% at 2 days and 78% at 3 days.

TABLE 3

| P. citricola | | | | P. citrophthora | | | |
|---|---|---|---|---|---|---|---|
| µM/ml MI | Days | Recovery % | Note | µM/ml MI | Days | Rceovery % | Note |
| 0 | 1 | 100 | a | 0 | 1 | 100 | a |
| 0 | 2 | 100 | a | 0 | 2 | 100 | a |
| 0 | 3 | 100 | a | 0 | 3 | 100 | a |
| 0.21 | 1 | 33 | b | 0.21 | 1 | 100 | a |
| 1.69 | 2 | 2 | c | 0.21 | 2 | 10 | b |
| 0.21 | 2 | 1 | c | 0.21 | 3 | 10 | b |
| 0.21 | 3 | 0 | c | 0.42 | 1 | 0 | c |
| 0.42 | 1 | 0 | c | 0.42 | 2 | 0 | c |
| 0.42 | 2 | 0 | c | 0.42 | 3 | 0 | c |
| 0.42 | 3 | 0 | c | 0.84 | 1 | 0 | c |
| 0.84 | 1 | 0 | c | 0.84 | 2 | 0 | c |
| 0.84 | 2 | 0 | c | 0.84 | 3 | 0 | c |
| 0.84 | 3 | 0 | c | 1.27 | 1 | 0 | c |
| 1.27 | 1 | 0 | c | 1.27 | 2 | 0 | c |
| 1.27 | 2 | 0 | c | 1.27 | 3 | 0 | c |
| 1.27 | 3 | 0 | c | 1.69 | 1 | 0 | c |
| 1.69 | 1 | 0 | c | 1.69 | 2 | 0 | c |
| 1.69 | 3 | 0 | c | 1.69 | 3 | 0 | c |
| 0 | 1 | 100 | a | 0 | 1 | 100 | a |
| 0 | 2 | 100 | a | 0 | 2 | 100 | a |
| 0 | 3 | 100 | a | 0 | 3 | 100 | a |
| 0.21 | 1 | 98 | a | 0.21 | 1 | 100 | a |
| 0.21 | 2 | 19 | b | 0.21 | 2 | 10 | a |
| 0.21 | 3 | 0 | b | 0.21 | 3 | 100 | a |
| 0.42 | 1 | 0 | b | 0.42 | 1 | 100 | a |
| 0.42 | 2 | 0 | b | 0.42 | 3 | 91 | ab |
| 0.42 | 3 | 0 | b | 1.69 | 3 | 78 | abc |
| 0.84 | 1 | 0 | b | 1.27 | 3 | 68 | bcd |
| 0.84 | 2 | 0 | b | 1.69 | 2 | 53 | cde |
| 0.84 | 3 | 0 | b | 0.84 | 3 | 45 | def |
| 1.27 | 1 | 0 | b | 0.84 | 2 | 44 | def |
| 1.27 | 2 | 0 | b | 1.27 | 2 | 43 | def |
| 1.27 | 3 | 0 | b | 0.42 | 2 | 32 | ef |
| 1.69 | 1 | 0 | b | 0.84 | 1 | 30 | efg |
| 1.69 | 2 | 0 | b | 1.69 | 1 | 20 | fg |
| 1.69 | 3 | 0 | b | 1.27 | 1 | 17 | fg |

Example 5

Alkyl iodides tested were MI, 1-iodoethane, 1-iodopropane, 2-iodopropane, 1-iodobutane, 1-iodopentane, diiodomethane, and 1-iodo-2-methylpropane. Inoculum was prepared and trials were performed as in Example 1. The chemicals were compared on a molar basis with rates of 1.27 and 0.42 µM/ml (equal to ¾ lb and ¼ lb MBr/100 ft³, respectively). The test organism was *Phytophthora parasitica*. Soil moisture was 24%. Fumigation exposure was 48 hours with 4 replications of 25 seeds each per treatment.

In this trial MI was the most effective compound with 0 recovery at both concentrations (1.27 and 0.42 µM/ml =to ¾ lb MBr and ¼ lb MBr/100 ft³). This was followed by diiodomethane with a 62% recovery at the high concentration. All other concentrations were not significantly different from the control (TABLE 4).

TABLE 4

| Chemical | µM/ml MI | % Survival | Note |
|---|---|---|---|
| None | 0 | 97 | a |
| 1-iodo-2-methyl-propane | 1.27 | 93 | a |
| 1-iodo-2-methyl-propane | 0.42 | 98 | a |
| 1-iodo-pentane | 1.27 | 92 | a |
| 1-iodo-pentane | 0.42 | 96 | a |
| 1-iodo-butane | 1.27 | 90 | a |
| 1-iodo-butane | 0.42 | 93 | a |
| 2-iodo-propane | 1.27 | 94 | a |
| 2-iodo-propane | 0.42 | 92 | a |
| 1-iodo-propane | 1.27 | 94 | a |
| 1-iodo-propane | 0.42 | 91 | a |
| 1-iodo-ethane | 1.27 | 81 | a |
| 1-iodo-ethane | 0.42 | 82 | a |
| Di-iodo-methane | 0.42 | 84 | a |
| Di-iodo-methane | 1.27 | 62 | b |
| Methyl iodide | 0.42 | 0 | c |
| Methyl iodide | 1.27 | 0 | c |

Example 6

The soil was prepared for this trial as in Example 5; soil moisture was 32%. Rates used were 1.27 and 0.42 µM/ml for MI and 2.54 and 1.27 µM/ml for all other chemicals. Fumigation exposure was 48 hours with 4 replications of 25 seeds each per treatment. MI was again the most effective compound with 0 recovery at both rates (1.27 and 0.42 µM/ml =to ¾ lb and ¼ lb/100 ft³). This was followed by 1-iodoethane at 2.54 µM/ml (=to 1.5 lb MBr/100 ft³). All other concentrations were not significantly different from the control.

TABLE 5

| Chemical | µM/ml MI | % Survival | Note |
|---|---|---|---|
| None | 0 | 98 | a |
| 1-iodo-2-methyl-propane | 2.54 | 100 | a |
| 1-iodo-2-methyl-propane | 1.27 | 100 | a |
| 1-iodo-pentane | 2.54 | 100 | a |
| 1-iodo-pentane | 1.27 | 100 | a |
| 1-iodo-butane | 2.54 | 100 | a |
| 1-iodo-butane | 1.27 | 100 | a |
| 2-iodo-propane | 2.54 | 99 | a |
| 2-iodo-propane | 1.27 | 100 | a |
| 1-iodo-propane | 2.54 | 100 | a |
| 1-iodo-propane | 1.27 | 100 | a |
| Di-iodo-methane | 2.54 | 100 | a |
| Di-iodo-methane | 1.27 | 100 | a |
| 1-iodo-ethane | 1.27 | 100 | a |
| 1-iodo-ethane | 2.54 | 0 | b |

TABLE 5-continued

| Chemical | μM/ml MI | % Survival | Note |
|---|---|---|---|
| Methyl iodide | 0.42 | 0 | b |
| Methyl iodide | 1.27 | 0 | b |

Example 7

This trial was a comparison of MI, diiodomethane and 1-iodoethane at 0.42, 0.84, 1.27, 1.69, and 2.11 μM/ml (equal to ¼, ½, ¾, 1 and 1 ¼ lb MBr/100 ft$^3$). *Phytophthora parasitica* was used as the test organism. Soil moisture was 32% with a fumigation time period of 48 hours. There were 4 replications per treatment. MI applications at all concentrations were the best treatments and were significantly different from all other treatments. This was followed by diiodomethane and 1-iodoethane at 2.11 and diiodomethane at 1.69 and 1.27 μM/ml. All other treatments were not significantly different from the control.

TABLE 6

| Chemical | μM/ml MI | % Survival | Note |
|---|---|---|---|
| None | 0 | 100 | a |
| Di-iodo-methane | 0.42 | 100 | a |
| Di-iodo-methane | 0.84 | 100 | a |
| 1-iodo-ethane | 0.42 | 100 | a |
| 1-iodo-ethane | 0.84 | 100 | a |
| 1-iodo-ethane | 1.27 | 100 | a |
| 1-iodo-ethane | 1.69 | 100 | a |
| Di-iodo-methane | 1.27 | 87 | b |
| Di-iodo-methane | 1.69 | 78 | bc |
| 1-iodo-ethane | 2.11 | 70 | c |
| Di-iodo-methane | 2.11 | 66 | c |
| Methyl iodide | 0.42 | 0 | d |
| Methyl iodide | 0.84 | 0 | d |
| Methyl iodide | 1.27 | 0 | d |
| Methyl iodide | 1.69 | 0 | d |
| Methyl iodide | 2.11 | 0 | d |

Example 8

The test soil for this field trial was a sandy loam averaging 5.85% moisture at 15 cm. The trial was a randomized block with 7 treatments of 4 replications each. The test organism was *Phytophthora parasitica* prepared as described above and incubated on the laboratory bench overnight before placement in the field. Fumigants used were MBr at 454, 227 and 113.5 g/9 m$^2$ (1, ½ and ¼ lb/100 ft$^2$) and MI at 684, 342 and 171 g/9 m$^2$ (1.5, 0.75 and 0.325 lb/100 ft$^2$). These rates are 4.8, 2.4 and 1.2 moles.

MI and MBr were similar in performance. There were low percentages of recovery in six fumigated plots. At 2.4M both MI and MBr had two plots with recovered organisms. MI had a 1 percent recovery at 4.8M and MBr had a 1 percent at 1.2M. The highest rate of recovery for MBr was 3% at 2.4M and a 12 inch depth, while for MI it was 4% at 2.4M at 6 inches. All controls were recovered at 100% (TABLE 7).

TABLE 7

| (field trial 1) | | | | |
|---|---|---|---|---|
| Chemical | M/100 ft$^3$ | Depth (in) | % Recovery | Note |
| Control | 0 | 1 | 100 | a |
| Control | 0 | 6 | 100 | a |

TABLE 7-continued

| (field trial 1) | | | | |
|---|---|---|---|---|
| Chemical | M/100 ft$^3$ | Depth (in) | % Recovery | Note |
| Control | 0 | 12 | 100 | a |
| MI | 2.4 | 6 | 4 | b |
| MBr | 2.4 | 12 | 3 | bc |
| MI | 2.4 | 1 | 2 | bc |
| MBr | 2.4 | 6 | 1 | bc |
| MI | 4.8 | 6 | 1 | bc |
| MI | 1.2 | 12 | 1 | bc |
| MBr | 1.2 | 1 | 0 | c |
| MBr | 1.2 | 6 | 0 | c |
| MBr | 1.2 | 12 | 0 | c |
| MBr | 2.4 | 1 | 0 | c |
| MBr | 4.8 | 12 | 0 | c |
| MI | 1.2 | 1 | 0 | c |
| MI | 1.2 | 6 | 0 | c |
| MI | 2.4 | 12 | 0 | c |
| MI | 4.8 | 1 | 0 | c |
| MI | 4.8 | 12 | 0 | c |
| MBr | 4.8 | 1 | 0 | c |
| MBr | 4.8 | 6 | 0 | c |

Example 9

In this field trial, soil moisture averaged 9.5% between 15 and 30 cm. MBr was applied as in Example 8. MI was mixed with 95% ethanol and poured in a cross pattern across the plot for better distribution. Fumigant rates were as in Example 5. The ethanol was mixed at 160, 80 and 40 ml for the high, medium and low rates, respectively. Controls were non-treated and ethanol at 160 ml/plot. Plots were fumigated for 4 days and aerated 1 day before plating.

MI and MBr were again similar in performance, although the percent recovery in fumigated plots ranged from 24 to 45% at rates of 1.2M for 4 plots (2 MI and 2 MBr) and 2.4M for one plot (MBr). Controls at 6 and 12 inch depths were recovered at 99 to 100%. All treatments at 1 inch depth had 0% recovery due to the effects of solarization (TABLE 8).

TABLE 8

| (field trial 2) | | | | |
|---|---|---|---|---|
| Chemical | M/100 ft$^3$ | Depth (in) | % Recovery | Note |
| Control | 0 | 6 | 100 | a |
| Control | 0 | 12 | 99 | a |
| Ethanol | 0 | 6 | 99 | a |
| Ethanol | 0 | 12 | 99 | a |
| MI | 1.2 | 12 | 45 | b |
| MBr | 2.4 | 12 | 25 | bc |
| MBr | 1.2 | 6 | 25 | bc |
| MBr | 1.2 | 12 | 25 | bc |
| MI | 1.2 | 6 | 24 | bc |
| MBr | 1.2 | 1 | 0 | c |
| MBr | 2.4 | 1 | 0 | c |
| MBr | 2.4 | 6 | 0 | c |
| MBr | 4.8 | 1 | 0 | c |
| MBr | 4.8 | 6 | 0 | c |
| MBr | 4.8 | 12 | 0 | c |
| MI | 1.2 | 1 | 0 | c |
| MI | 2.4 | 1 | 0 | c |
| MI | 2.4 | 6 | 0 | c |
| MI | 2.4 | 12 | 0 | c |
| MI | 4.8 | 1 | 0 | c |
| MI | 4.8 | 6 | 0 | c |
| MI | 4.8 | 12 | 0 | c |
| Control | 0 | 1 | 0 | c |
| Ethanol | 0 | 1 | 0 | c |

Example 10

The effects of MI fumigation on three weed seeds were determined. The percent survival of these seed after fumigation with different concentrations of MI is reported in TABLE 9. The percent survival is calculated by dividing the number of treated germinated seeds by the number of untreated germinated seeds.

TABLE 9

| Treatment | Weed Species | | |
|---|---|---|---|
| μM/ml MI | Annual Bluegrass | Cheeseweed | Field Bindweed |
| 1.69 | 0 | 0 | 3.6 |
| 1.27 | 0 | 0 | 1.8 |
| 0.84 | 0 | 0 | 0 |
| 0.42 | 0 | 0 | 1.8 |
| 0.21 | 0 | 0 | 5.4 |

Example 11

The effects of MI treatment on the nematode *Meloidogyne incognita* were determined. The percent survival after fumigation at different concentrations of MI are reported in TABLE 10. The percent survival was calculated by dividing the number of treated surviving nematodes by the number of untreated surviving nematodes.

TABLE 10

| μM/ml MI | percent survival |
|---|---|
| 0.052 | 0 |
| 0.026 | 0 |
| 0.013 | 0 |
| 0.006 | 55 |
| 0.003 | 65 |

Example 12

The effects of MI on the citrus nematode *Tylenchulus semipenetrans* were determined. The numbers surviving after fumigation at different concentrations of MI are reported in TABLE 11.

TABLE 11

| Rate (lb/ac - μM/container) | Mean | Fisher's protected LSD p = .05 |
|---|---|---|
| 25 lb/ac (0.95 μM) | 0.000 | a |
| 15 lb/ac (0.57 μM) | 0.250 | a |
| 5 lb/ac (0.19 μM) | 4.000 | a |
| 2 lb/ac (.072 μM) | 64.750 | b |
| 0 lb/ac (0 μM) | 223.000 | c |

Example 13

The effects of MI, MBr, clear and black plastic covers on survival of weeds in the soil were examined.

TABLE 12

| Plastic[1] | No Treatment | Methyl Bromide[2] | Methyl Iodide |
|---|---|---|---|
| None | 2[3] | Not used | Not used |
| Clear | 1.5 | 4.75 | 5 |
| Black | 2.25 | 4.75 | 4.5 |

[1]4 mil thick.
[2]Methyl bromide and methyl iodide were used at 4.8 M/100 ft$^2$.
[3]Rating 1–5: 1 = dense weed population; 5 = no weeds.

Example 14

Fumigation of Termites Using MBr

Pseudergates ("workers") of the West Indian powderpost drywood termite, *Cryptoteryes brevis* (*C. brevis*) (Walker) were exposed in the laboratory to various concentrations of gaseous MI at 27° C. for 20 hours. Threshold for 100% mortality of *C. brevis* was determined to be between 48 and 60 mg hr/L (=oz hr/1,000 ft$^3$).

*C. brevis* is the most destructive drywood termite pest worldwide. In the United States, this pest is often controlled by structural fumigation using either MBr or sulfuryl fluoride. This preliminary study was conducted to determine if MI is toxic to *C. brevis* under laboratory conditions.

Materials and Methods

*C. brevis* pseudergates were harvested from solid wood doors collected at Key West, Fla., in December. Termites were maintained in the laboratory in containers provisioned with Pinus spp. wood slats. Individual groups of 20 termites were placed on 47-mm o.d. filter paper pads set in the bottoms of glass petri dishes (50 mm i.d.) and covered with lids.

Five 9-liter glass desiccators were used a s fumigation chambers. First-round exposures were conducted at 0, 2, 4, 8, and 16 mg/L MI to identify a range of accumulated doses that yielded complete and no mortality for some of the termite groups. Based on that result, a second round of exposures was conducted to more closely identify a 100% mortality threshold concentration for MI.

Each fumigation round consisted of simultaneously exposing groups of pseudergates to five concentrations of MI. A dish with termites was placed in each chamber before chambers were sealed with silicone vacuum crease. Four doses of MI and an untreated (air) control were consecutively introduced into separate chambers every 5 min. Neat MI liquid (99% iodomethane, density 2.28 mg/μL; Aldrich Chemical #1-850-7 [74-88-4], Aldrich Chemical Company, Inc., Milwaukee, Wis., U.S.A.) was injected with a 10 or 100 μL syringe directly into the septum port of each chamber at the desired concentration while the air inside each chamber was stirred with a magnetic stirring propeller. All fumigations were conducted at 27±0.5° C. for 20 hours. After chamber aeration, dead or moribund individuals were recorded and removed daily until latent mortality had ceased (≦4 days).

Results

The first round exposures yielded complete mortality at all concentrations of MI except 2 mg/L by 3-day postexposure (TABLE 13). This dictated second round exposure concentrations of 0, 1.8, 2.4, 3.0, and 3.6 mg/L MI. These yielded 100% mortality at the two highest concentrations by day 3 (TABLE 13). No control mortality was observed. Therefore, under these conditions, MI will provide 100% control of *C. brevis* pseudergates at a Lethal Accumulated Dose$_3$ (LAD$_{100}$) of between 48 and 60 mg hr/L (=oz hr/1,000 ft$^3$) or 2.4 to 3.0 oz/1,000 ft$^3$ for a 20 hour exposure. This closely approximates the toxicities of MBr and sulfuryl fluoride against drywood termites.

TABLE 13

Exposure Concentrations and Percent Mortality (n = 1, 3 days post-exposure) of *Cryptotermes brevis* Pseudergates Exposed to Methyl Iodide for 20 Hours at 27° C.

| Conc. (mg/L) | Accumulated Dose (mg · hr/L) | Percent Mortality |
|---|---|---|
| *Round 1* | | |
| 0.0 | 0 | 0 |
| 2.0 | 40 | 15 |
| 4.0 | 80 | 100 |
| 8.0 | 160 | 100 |
| 16.0 | 320 | 100 |
| *Round 2* | | |
| 0.0 | 0 | 0 |
| 1.8 | 36 | 15 |
| 2.4 | 48 | 55 |
| 3.0 | 60 | 100 |
| 3.6 | 72 | 100 |

Example 15
Fumigation of Termites Using MBr

For these trials, the termite (*Incisitermes minor* (Hagen)) was used as the test organism using MBr and MI. Ten termites were placed on filter paper in 35 mm plastic petri plates. The top half of each plate had a 15 mm square hole covered by a fine screen for air and gas passage. The plates containing termites were placed into 1.893 liter canning jars (in a horizontal position) and a small evaporating dish was placed just inside the jar. The test materials were pipetted into the evaporating dish and the jars were sealed with a lid and ring. MI was used at room temperature. In the case of MBr, the evaporating dishes and pipette tips used with the MBr, were chilled using frozen $CO_2$ (at -56° C.) before use. Fumigation time was 20 hours. After fumigation, the jars were opened and the termites were removed for evaluation. Counts of dead termites were made over several days until no more were found dead. In some trials, the internal air was agitated using a magnetically driven spin bar. Two series of trials were run. In the first series, concentrations of MI or MBr ranged from 0.008 mM to 0.24 mM. In the second series, the concentrations ranged from 0.02 to 0.036 mM.

Results:

The results of the two series tests are shown in TABLES 14–15 below. In each trial, for each methyl halogen, four replications of tests (each test involving 10 termites) were conducted, totaling 40 termites. The number of killed termites are listed in the TABLES.

TABLE 14

First Series.

| Conc. | Trial 1 | | Trial 2 | | Trial 3 | | Trial 4 | |
|---|---|---|---|---|---|---|---|---|
| mM | MBr | MI | MBr | MI | MBr | MI | MBr | MI |
| 0 | 0.0 a | 0.0 a | 0.0 a | 0.0 a | 0.2 a | 0.2 a | 0.2 a | 0.2 a |
| 0.008 | 0.0 a | 2.5 b | 7.7 cd | 3.0 ab | 8.7 c | 0.2 a | 2.7 a | 0.5 a |
| 0.012 | 2.7 b | 8.2 c | 5.5 bc | 3.0 ab | 8.7 c | 0.2 a | 5.5 b | 1.0 a |
| 0.016 | 8.5 c | 9.0 c | 8.5 cd | 8.0 cd | 5.5 bc | 1.0 ab | 9.2 c | 2.4 a |
| 0.02 | 9.0 c | 10.0 c | 10.0 d | 9.7 d | 4.2 abc | 5.0 bc | 9.0 c | 7.7 bc |

TABLE 14-continued

First Series.

| Conc. | Trial 5 | | Trial 6 | | Trial 7 | |
|---|---|---|---|---|---|---|
| mM | MBr | MI | MBr | MI | MBr | MI |
| 0 | 0.0 a | 0.0 a | 0.0 a | 0.0 a | 0.0 a | 0.0 a |
| 0.008 | 0.7 ab | 0.5 ab | 4.7 bcd | 1.2 ab | 8.3 b | 0.0 a |
| 0.012 | 6.5 d | 1.5 ab | 6.0 d | 0.5 ab | 10.0 b | 0.0 a |
| 0.016 | 7.2 de | 3.2 bc | 5.7 cd | 1.5 abc | 3.3 a | 3.0 a |
| 0.02 | 9.2 de | 6.2 cd | 5.0 d | 4.2 abcd | 8.0 b | 8.0 b |
| 0.024 | 10.0 e | 6.5 d | 7.0 d | 8.2 d | 7.5 b | 9.5 b |
| 0.028 | | | | | 10.0 b | 9.7 b |

TABLE 15

Second Series.

| Conc. | Trial 8 | | Trial 9 | |
|---|---|---|---|---|
| mM | MBr | MI | MBr | MI |
| 0 | 0.0 a | 0.0 a | 0.0 a | 0.0 a |
| 0.02 | 10.0 c | 7.7 b | 6.5 b | 1.0 a |
| 0.024 | 10.0 c | 9.7 c | 8.5 bcd | 7.0 bc |
| 0.028 | 9.7 c | 9.7 c | 9.5 cd | 9.5 cd |
| 0.032 | 10.0 c | 10.0 c | 8.7 bcd | 10.0 d |
| 0.036 | 10.0 c | 10.0 c | 10.0 d | 10.0 d |

\* Numbers within each trial followed by the same letter are not significantly different according to the Waller-Duncan multiple range test (P = 0.05).

From the above trials it is quite apparent that both chemicals are variable and inconsistent in their ability to kill the termites at concentrations ranging from 0.008 to 0.02 mM. At 0.024 mM concentrations to 0.036 mM. both chemicals become more reliable in killing the termites with achieving an average 96% kill at 0.028 mM and 100% at 0.036 mM concentrations.

TABLE 16

Conversion from molar to pounds per 1000 cubic feet.

| Concentration | milligrams per liter (mg/L) | | pounds per 1000 cubic feet | |
|---|---|---|---|---|
| mM | MBr | MI | MBr | MI |
| 0.008 | 0.76 | 1.14 | 0.05 | 0.07 |
| 0.012 | 1.14 | 1.70 | 0.07 | 0.11 |
| 0.016 | 1.52 | 2.27 | 0.09 | 0.14 |
| 0.02 | 1.90 | 2.84 | 0.12 | 0.18 |
| 0.024 | 2.28 | 3.41 | 0.14 | 0.21 |
| 0.028 | 2.66 | 3.95 | 0.17 | 0.25 |
| 0.032 | 3.04 | 4.54 | 0.19 | 0.28 |
| 0.036 | 3.42 | 5.11 | 0.21 | 0.32 |

For comparison 1 pound (454,000 mg) of methyl bromide per 1000 cubic feet (28,320 liters) equals 16.031 milligrams per liter or a 0.169 mM concentration.

From the above it can be readily seen that killing of termites can be achieved at extremely low concentrations. Commercial applications for MBr fumigation are in the range of one-half to two pounds per 1000 cubic feet. From the above data, efficacy is found at as low as 3 oz per 1000 cubic feet. From a practical standpoint, these concentrations would likely be ineffective due to difficulties in even distribution and losses through the covering tarps etc.

Example 16
Fumigation of the Dry Wood Rotting Fungi *Meruliporia incrassata* and *Gleophyllum separium*.

The fumigation chamber used for these trials is the same as that used for termites in EXAMPLE 15, above. In one method, the fungi were grown in petri plates on potato dextrose agar. When used for trials, 3 mm disks were cut from the leading edge of fungi growth and placed on one half of a small petri plate. The plates were then placed in the fumigation chambers and treated as described in EXAMPLE 15, above. In the second method, the only difference was that the fungi were grown on sterile millet seed, mixed with sterile soil and placed in perforated vials before being placed in the fumigation chamber. (Both methods gave similar results. Results generated by tests on the infected millet seed are reported here.)

After fumigation, the fungal disks or infected seeds were placed on water agar to detect growth. There were four replications per treatment with 10 disks or seeds used per replication.

TABLE 17

Results: *Meruliporia incrassata* (Data expressed as the average number of seed having fungal growth after treatment).
nt = concentration not used in this trial.

| Conc. | Trial 1 | | Trial 2 | | Trial 3 | |
|---|---|---|---|---|---|---|
| mM | MBr | MI | MBr | MI | MBr | MI |
| 0 | 10.0 a | 10.0 a | 10.0 a | 9.2 a | 10.0 a | 10.0 a |
| 0.0525 | 10.0 a | 10.0 a | 9.0 ab | 8.5 ab | nt | nt |
| 0.105 | 9.2 a | 7.2 b | 8.5 ab | 6.7 bc | 10.0 a | 9.7 a |
| 0.1575 | nt | nt | 6.7 bc | 6.0 cd | nt | nt |
| 0.21 | 7.0 b | 0.7 c | 2.2 efg | 3.7 de | 9.2 a | 8.5 a |
| 0.315 | nt | nt | 0.7 fg | 3.0 ef | 9.5 a | 2.7 c |
| 0.42 | 0.0 c | 0.0 c | 0.7 fg | 3.0 ef | 5.0 b | 1.7 cd |
| 0.525 | nt | nt | nt | nt | 1.7 cd | 0.0 e |
| 0.63 | nt | nt | nt | nt | 0.0 e | 0.2 de |
| 0.735 | nt | nt | nt | nt | 0.0 e | 0.0 e |
| 0.84 | 0.0 c | 0.0 c | 0.0 g | 0.0 g | 0.0 e | 0.0 e |

TABLE 18

*Gleophyllum separium* (Data expressed as the average number of seed having fungal growth after treatment).
nt = concentration not used in this trial.

| Conc. | Trial 1 | | Trial 2 | | Trial 3 | |
|---|---|---|---|---|---|---|
| mM | MBr | MI | MBr | MI | MBr | MI |
| 0 | 10.0 a | 10.0 a | 10.0 a | 10.0 a | 10.0 a | 9.7 a |
| 0.0525 | 10.0 a | 10.0 a | 10.0 a | 10.0 a | nt | nt |
| 0.105 | 10.0 a | 10.0 a | 9.7 a | 9.7 a | 10.0 a | 9.7 a |
| 0.1575 | nt | nt | 9.7 a | 8.5 a | nt | nt |
| 0.21 | 10.0 a | 8.2 ab | 10.0 d | 5.5 b | 10.0 a | 9.0 a |
| 0.315 | nt | nt | 10.0 a | 5.7 b | 9.7 a | 2.5 b |
| 0.42 | 7.2 b | 0.2 c | 2.7 c | 5.7 b | 2.0 bc | 1.2 cd |
| 0.525 | nt | nt | nt | nt | 0.0 e | 0.0 e |
| 0.63 | nt | nt | nt | nt | 0.2 de | 0.0 e |
| 0.735 | nt | nt | nt | nt | 0.2 de | 0.0 e |
| 0.84 | 0.0 c | 0.0 c | 0.0 d | 0.0 d | 0.0 e | 0.0 e |

Results of fumigations of the two wood rotting fungi *Meruliporia incrassata* and *Gleophyllum separium* show that at concentrations of 0.21 mM and below neither fumigant is effective in controlling the two fungi. However, at concentrations of 0.315 mM and above, both chemicals show effectiveness with methyl iodide having the most consistent effectiveness and both achieving complete kill by 0.84 mM.

TABLE 19

| Conversion from molar to pounds per 1000 cubic feet | | | | |
|---|---|---|---|---|
| Concentration | milligrams per liter (mg/L) | | pounds per 1000 cubic feet | |
| mM | MBr | MI | MBr | MI |
| 0.052 | 4.98 | 7.45 | 0.31 | 0.46 |
| 0.105 | 9.97 | 14.90 | 0.62 | 0.93 |
| 0.157 | 14.95 | 22.36 | 0.93 | 1.40 |
| 0.21 | 19.94 | 29.81 | 1.24 | 1.86 |
| 0.31 | 29.91 | 44.71 | 1.87 | 2.79 |
| 0.42 | 39.88 | 59.62 | 2.49 | 3.72 |
| 0.52 | 49.85 | 74.52 | 3.11 | 4.65 |
| 0.63 | 59.82 | 89.43 | 3.73 | 5.58 |
| 0.73 | 69.79 | 104.33 | 4.36 | 6.51 |
| 0.84 | 79.76 | 119.64 | 4.98 | 7.47 |

It can readily be seen from comparing the data and the two charts that the concentrations required to kill the fungi are much higher than those for termites.

Lyctid eggs were fumigated the same as termites in EXAMPLE 15, above, but the number of eggs available was quite small. In the tests that were completed, the lowest concentration of MBr (0.004 mM) had 8 surviving eggs out of 20 fumigated. There were no survivors at 0.008 and 0.016 mM. Those eggs treated with MI were completely killed with no survivors.

While the present invention has been described with reference to preferred embodiments and illustrative examples, it should be understood that one of ordinary skill in the art after reading the foregoing specification would be able to effect various changes, substitutions of equivalents and modifications to the methods as described herein. Therefore, it is intended that the scope of the invention not be limited by reference to the illustrative examples, but rather with reference to the accompanying claims.

What is claimed is:

1. A method for structural fumigation, comprising:

applying to a structure an effective amount of methyl iodide.

2. The method of claim 1, wherein the effective amount is between about 3 oz per 1000 cubic feet and about 100 lb per 1000 cubic feet.

3. The method of claim 2, wherein the effective amount is between about 8 oz per 1000 cubic feet and about 50 lb per 1000 cubic feet.

4. The method of claim 3, wherein the effective amount is between about 1 lb per 1000 cubic feet and about 10 lb per 1000 cubic feet.

5. The method of claim 1, wherein methyl iodide is applied in combination with at least one additional fumigant.

6. The method of claim 5, wherein the additional fumigant is carbon disulfide or chloropicrin.

7. The method of claim 1, wherein the methyl iodide is preheated prior to application.

8. The method of claim 1, wherein the structure is tarped during application.

9. The method of claim 1, wherein the methyl iodide is applied in combination with carbon dioxide.

\* \* \* \* \*